United States Patent [19]

Ross et al.

[11] 4,343,048
[45] Aug. 10, 1982

[54] STENT FOR A CARDIAC VALVE

[76] Inventors: Donald N. Ross, 25 Upper Wimpole St., London W.1; Endre Bodnar, 9 West End Ct., West End Ave., Pinner, Middlesex; William J. Hoskin, 5 Long Buftlers, Harpenden, Hertfordshire, all of England

[21] Appl. No.: 175,083

[22] Filed: Aug. 4, 1980

[30] Foreign Application Priority Data

Aug. 6, 1979 [GB] United Kingdom ................. 7927293

[51] Int. Cl.³ .............................................. A61F 1/22
[52] U.S. Cl. ....................................................... 3/1.5
[58] Field of Search ........................................ 3/1.5, 1

[56] References Cited

U.S. PATENT DOCUMENTS

| | | | |
|---|---|---|---|
| 3,503,079 | 3/1970 | Smith | 3/1.5 |
| 3,570,014 | 3/1971 | Hancock | 3/1.5 |
| 3,601,877 | 8/1971 | Goosen | 3/1.5 X |
| 3,739,402 | 6/1973 | Cooley et al. | 3/1.5 |
| 3,755,823 | 9/1973 | Hancock | 3/1.5 |
| 4,106,129 | 8/1978 | Carpentier et al. | 3/1.5 |
| 4,276,132 | 6/1981 | Fettel et al. | 3/1.5 X |

FOREIGN PATENT DOCUMENTS

| | | | |
|---|---|---|---|
| 1243293 | 8/1971 | United Kingdom | 3/1.5 |
| 1264471 | 2/1972 | United Kingdom | 3/1.5 |

OTHER PUBLICATIONS

"Reconstruction Heterograft Aortic Valves for Human Use", by M. I. Ionescu et al., Thorax, 23, No. 3, May 1968, pp. 221–229.

Primary Examiner—Ronald L. Frinks
Attorney, Agent, or Firm—Stevens, Davis, Miller & Mosher

[57] ABSTRACT

A stent for a cardiac valve comprises a metal base ring having metal legs projecting therefrom in a generally axial direction, each leg being flexible in such a manner that, when the stent has a valve installed therein and the valve is under pressure such as when operating in the heart, each respective leg can resiliently deform over substantially its whole axial length to take up strain in the valve without impairing its performance.

21 Claims, 4 Drawing Figures

U.S. Patent  Aug. 10, 1982  4,343,048
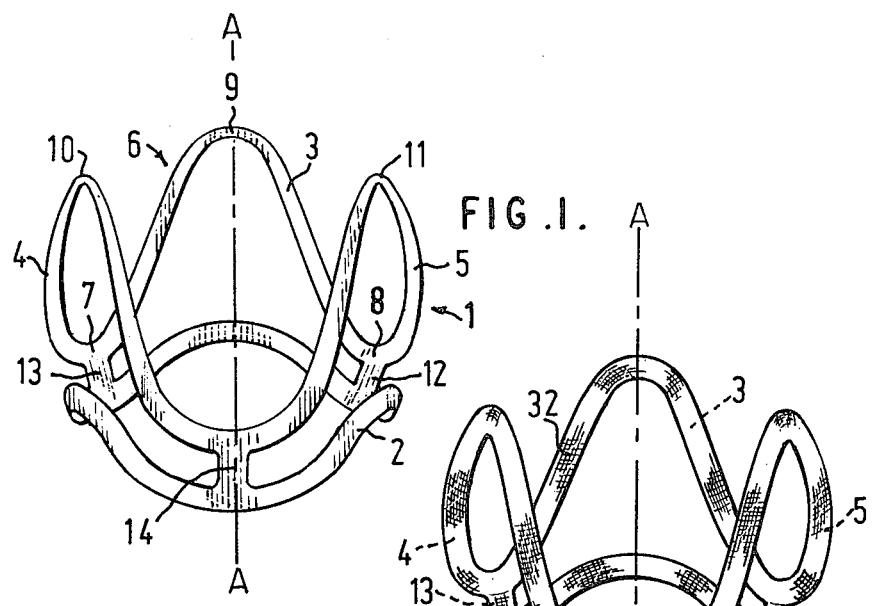
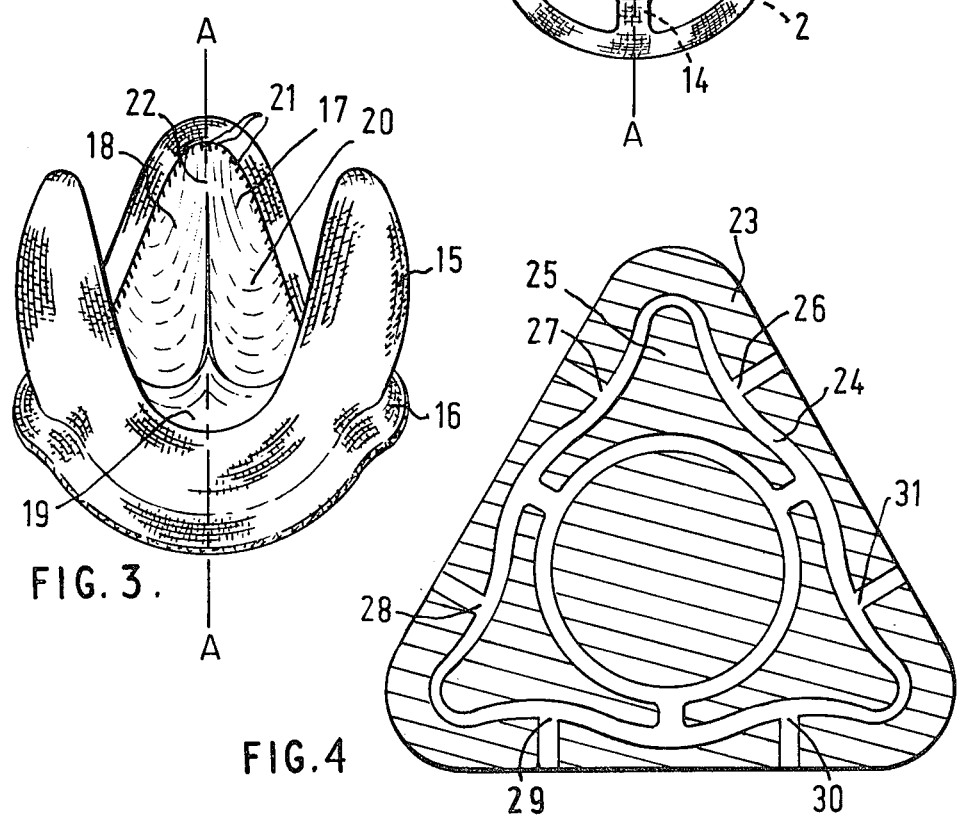

STENT FOR A CARDIAC VALVE

This invention relates to a stent for a cardiac valve.

Aortic and pulmonary valves of human or animal origin can be used for the replacement of defective cardiac valves. If the transplanted valve is non-viable, i.e. has been fixed and preserved in chemicals, it has to be supported in a frame, which is known as a stent. Stents can also be used to support bioprosthetic cusped valves fabricated from fixed natural tissue such as pericardium.

The present invention is concerned with a kind of stent (herein referred to as a stent of the kind defined) which comprises a metal base ring having metal legs projecting therefrom in a generally axial direction. In known forms, stents of the kind defined are generally cloth covered. Also, for use in certain locations, stents of the kind defined may have a suture ring around the external periphery of the base ring. The non-viable valve is mounted within, and attached to, the stent, the valve being oriented such that its commissures are supported by the legs; thus, the direction of blood flow through the valve will be generally in the direction in which the legs of the stent extend. As the valve is entirely within the stent, the size of valve which can be accommodated at a given location in the heart using a stented valve will be smaller than would have been the case using a similar but non-stented valve.

For a person whose average pulse rate is 80 per minute, the heart beats over forty million times in a year. It will therefore be readily appreciated that a stented cardiac valve, if it is not to fail in service, must be capable of withstanding the repeated application of the stresses to which it is subject when in operation when installed in the heart. A particular danger which must be guarded against as far as possible is that of rupture of the valve in the region of the commissures of the valve cusps.

U.S. Pat. No. 3,755,823 (Hancock) discloses a stent of the kind defined. With a view to reducing the aforementioned danger, the stent disclosed by Hancock in all of its disclosed forms has legs which are so attached to the base ring that when under load (when in the closed position) they can lean inwardly towards the valve axis, the base ring undergoing torsional distortion. This is said to reduce the tensile stress in the region of the commissures of the valve cusps by approximately 20 percent. In the stent disclosed by Hancock, the stress absorbed by the stent is applied over relatively small areas adjacent to the points of attachment of the legs to the base ring, thus giving rise to the risk of failure, as a result of fatigue, of the stent in those areas. Of course this risk can be counteracted by suitable strengthening of the stent, but this leads to increased bulk in the stent, which clearly is undesirable.

According to the present invention, there is provided a stent for a cardiac valve, the stent comprising a metal base ring having metal legs projecting therefrom in a generally axial direction, each said leg being flexible (as herein defined).

The term "flexible" as used herein in relation to the legs of a stent in accordance with the invention means that each respective leg is such that, when the stent has a valve installed therein and the valve is subjected to pressure conditions such as those to which it would be subjected when installed within a heart, the leg can resiliently deform over substantially its whole axial length to an extent sufficient to take up strain in the valve without substantially impairing its performance. Generally, the flexibility of each leg should be such that, in order to move the end of the leg remote from the base ring a distance of 1 mm towards the valve axis, it is necessary to apply to that end of the leg a radial load (i.e. a load directed towards the valve axis) which lies within the range 50 g to 150 g. Preferably the load required to achieve such deflection is within the range 70 g to 90 g.

As will be appreciated from the following description, it is possible in accordance with the invention to provide a stent which, while able when installed, with a valve mounted therein, in a heart resiliently to yield to take some of the strain of operation from the valve, need not be made unduly bulky in order to permit this to be achieved without importing an unreasonable risk of failure of the stent in operation. Furthermore, the manner of this yielding can closely approximate to the manner in which natural valves are permitted reversibly to deform by the nature of the natural supporting structure therefor (e.g. the support provided in nature by the aorta for the aortic valve).

We very much prefer that the base ring of the stent of the present invention should be substantially rigid, by which we mean that, when the stent has a valve installed therein and the valve is subjected to pressure conditions such as those to which it would be subjected when installed within a heart, the base ring should not deform to any substantial extent. We believe that rigidity of the base ring is important to guard against unnatural distortion of the valve in use such as would impair proper sealing of the valve cusps.

A preferred metal for the metal base ring and metal legs is an alloy known as titanium 6Al 4V (the figures representing the respective weight percentages of aluminium and vanadium). We have found that this alloy has very good properties for the present purpose; as well as combining lightness with strength, it is biocompatible, and it has very little elastic memory.

In accordance with a preferred embodiment, each leg is so shaped that, as it projects from the base ring, it curves inwardly towards the axis of the stent. This enables us to use a particularly lightweight construction while at the same time providing the required combination of flexibility and strength. We term this the "fishing rod structure", and believe that the reason for the advantages just mentioned are similar to those responsible for the somewhat similar properties found in good quality fishing rods.

A form of construction which we particularly prefer is one in which a length of metal smoothly rises and falls around the circumference of the stent so as to define the outline of each successive metal leg. This can provide an especially lightweight construction. Also, as will be seen later, this construction can enable a relatively large size of valve to be accommodated within a given size of stent, especially when combined with the shape of leg referred to in the previous paragraph. The thickness of the aforementioned length of metal preferably varies such that it smoothly decreases as it rises away from the base ring and smoothly increases as it falls towards the base ring. We have found that this feature can enable a valve fitted to the stent to deform when under load in a manner which is particularly similar to the deformation experienced by a natural valve in operation.

The aforementioned length of metal is preferably structurally connected to the base ring (by which we mean to exclude indirect connection by items such as cloth coverings for the stent) solely by a connection between the base ring and the length of metal at each of the points of closest approach of the length of metal to the base ring. By this means, the base ring can be made substantially rigid with a relatively lightweight construction.

Preferably the aforementioned length of metal is cloth-encased, as this can help in the construction of a stent in which the marginal portions of the valve to be supported by the legs do not lie closer to the valve axis than the innermost portions of the legs themselves. Generally, all other lengths of metal in the valve stent, such as the base ring and any connections between the base ring and the legs, will also be cloth-encased.

In normal circumstances, the outer periphery of the stent will be cloth-covered, and for use in certain locations a suture ring will be provided around the outer periphery, adjacent to the base ring. These features, and also ways of incorporating them, are known per se.

Our research work has shown that, in order to decrease the risk of structural failure of the stent it is highly desirable that the metal assembly comprising the metal base ring and the metal legs should be monolithic; and for this purpose it is especially desirable that the metal assembly should be free of all joints such as welds. We have found that joints, unless made unduly bulky, always incorporate some degree of risk. Even with the most carefully made weld inspected so as to reveal even internal flaws, there is always the risk of an adverse variation in material or material properties.

A suitable process for making the aforementioned metal assembly in joint-free form comprises producing a blank, and forming the blank into the required shape. The blank may be produced from a sheet of the metal, or from a tube of the metal. Where the blank is produced from a sheet, it can be produced by a photoresist process or by stamping, for example. Cutting can be used to produce blanks from tubes as well as from sheets. We have found that particularly accurate cutting can be produced with a spark erosion device or with a laser cutter. These devices can, when the blank is cut from a sheet, be used to cut a plurality of substantially identical blanks simultaneously; for example, using a spark erosion device, we have found that 25 blanks can be cut in this way. Especially accurate, and reproducible, cutting can be achieved using computer-control for a spark erosion device or laser cutter.

Conveniently, suitably shaped male and female mold members may be used in forming the blank. Where the preferred titanium 6Al 4V alloy is used, the forming is preferably carried out at 950° C. ±50° C., and is preferably performed within an inert atmosphere to avoid risk of surface hardening and oxidation.

In order that the invention may be more fully understood, a preferred embodiment in accordance therewith will now be described with reference to the accompanying drawings, wherein:

FIG. 1 is a perspective view of a metal assembly comprising a metal base ring and metal legs;

FIG. 2 is a perspective view of the assembly of FIG. 1. after it has been cloth-encased;

FIG. 3 is a perspective view of a complete stent in accordance with the invention, after a valve has been fitted therein; and FIG. 4 is a plan view illustrating an intermediate stage in the manufacture of a blank suitable for making the assembly of FIG. 1.

The metal assembly 1 shown in FIG. 1 comprises a metal base ring 2 and legs 3, 4 and 5 and is intended for use with a valve which has three cusps, for example a natural aortic or pulmonary valve. While the metal assembly 1 is itself a stent, in that it could be used on its own to support a valve, it would not normally be used in such a basic form. Usually the stent will be cloth-covered, for example in the manner to be described with reference to FIGS. 2 and 3.

In each of FIGS. 1 to 3, the axis of the metal assembly 1 (and of the valve also, in the case of FIG. 3) is indicated by the line A—A. Each of legs 3, 4 and 5 projects from the base ring 2 generally in the direction of axis A—A, and is so shaped that, as it so projects, it curves inwardly towards axis A—A. This makes the overall shape of the assembly 1 somewhat barrel-like, and provides the individual legs with the "fishing rod structure" referred to earlier.

The legs 3, 4 and 5 are formed by a length of metal, indicated generally at 6, which smoothly rises and falls around the circumference of the assembly 1. It will be seen that each leg directly abuts each of its neighbours; there are no connecting pieces. Thus, for example, leg 3 abuts leg 4 at 7 and abuts leg 5 at 8. Also, the way in which the length of metal 6 smoothly rises and falls gives rise to a smooth tapering of each of legs 3, 4 and 5 towards their respective ends 9, 10 and 11 remote from the base ring 2. In order to control the flexibility of the legs along their lengths so that their resilient deformation in use will be distributed evenly along their axial lengths, the thickness of the length of metal 6 varies such that it smoothly decreases as it rises away from the base ring 2 and smoothly increases as it falls towards the base ring. Thus, for example, on leg 3 the thickness smoothly decreases from 7 to 9 and increases from 9 to 8.

Legs 3, 4 and 5 are structurally connected to base ring 2 solely by connecting lengths of metal 12, 13 and 14, at the points of closest approach of the length of metal 6 to the base ring 2.

It will be seen that the length of metal 6 has a scalloped configuration, and that the base ring 2 is also scalloped about its periphery, the scallops in base ring 2 being adjacent to those in length 6, but of substantially smaller magnitude.

The metal assembly 1, consisting of base ring 2, legs 3, 4 and 5 and connecting lengths 12, 13 and 14, is monolithic and joint-free.

FIG. 2 shows the metal assembly 1 after base ring 2, legs 3, 4 and 5 and connecting lengths 12, 13 and 14 have been cloth-encased as shown at 32; i.e. they are now located within respective tubes of cloth. A suitable material for this purpose is a knitted polyethylene terephthalate fabric such as the medical grade of fabric available under the registered Trade Mark "Dacron".

After the stage shown in FIG. 2, a generally tubular cloth cover (shown at 15 in FIG. 3) of polyethylene terephthalate fabric, for example, and also, if required for the location in the heart in which the device is ultimately to be used, a suture ring (shown at 16 in FIG. 3), is or are attached around the outer periphery of the stent, the cover initially having its axial ends projecting beyond the corresponding axial ends of the stent. A valve (shown at 17 in FIG. 3) having three cusps 18, 19 and 20 is then fixed within the lumen of the stent, and then the axial ends of the cover 15 are folded over the respective ends of the stent, trimmed so as slightly to overlap the respective axial ends of the valve and then fixed by suturing; some of the sutures around the downstream axial end of the valve 17 can be seen at 21 in FIG. 3. At this stage, one has the complete stent-mounted valve shown in FIG. 3.

The valve 17 can be a natural valve such as the aortic valve of a pig; or it may be any other suitable biomaterial, for example, pericardium. It will be seen that, owing to the inwardly curving shape and open structure of the legs 3, 4 and 5 of the metal assembly 1 at the heart of the stent, it has been possible to arrange that the commissure of the valve shown at 22 is somewhat recessed into the leg 3 (in its cloth-covered form) rather than being spaced inwardly (i.e. towards axis A—A) of the leg, as would have been the case in the absence of these two features. Of course, although they are not visible in FIG. 3, the other two commissures are similarly recessed, in legs 4 and 5 respectively. By virtue of this arrangement, it is possible to accommodate within the stent a valve of larger diameter (and thus one which is less restrictive of blood flow) than would otherwise have been the case.

The stent-mounted valve shown in FIG. 3 is intended to be surgically installed in a heart so as to permit the flow of blood through it upwardly as shown in the drawing, and to resist flow in the reverse direction. When the valve 17 is under load in its closed condition, the legs 3, 4 and 5 bend over their whole axial lengths, towards the axis A—A, thereby relieving strain on the valve, especially at the commissures 22, etc. We have found that owing to the laboriously designed shape of the legs 3, 4 and 5 of the metal assembly 1, the flexibility of the legs closely simulates the yielding experienced by natural valves during operation in their original environment. This is assisted by the fact that the base ring 2 is substantially rigid. Also, because the resilient deformation of the legs is spread over their whole axial lengths, there are no relatively highly stressed areas.

We will now describe a relatively simple procedure by which the metal assembly shown in FIG. 1 can be produced with the required accuracy. Firstly a blank is produced, by a photoresist process, from a sheet of the metal required for the metal assembly 1, the metal which we at present prefer being titanium (6Al 4V. A sheet of the metal (shown at 23 in FIG. 4) is cleaned, etched, coated with a photoresist emulsion and exposed to a suitable UV light image, so that the UV light strikes the sheet in the area comprising the shape required for the blank, i.e. the unshaded continuous area 24. This causes the emulsion to harden in that area, and the sheet is then treated with a liquid which selectively dissolves off the unhardened emulsion in the remaining areas, i.e. the areas 25 which are indicated by shading. The sheet is then etched in acid, typically 90% hydrofluoric, 10% nitric, so as to dissolve away areas 25, and is then deburred, examined for flaws and imperfections and is cut out from the frame (not shown) in which it is held, by cutting at 26, 27, 28, 29 30 and 31, to produce the blank.

Next, the blank is placed over a male mold member (forming mandril) in the form of a stainless steel cone which is heated to 950° C. ±50° C. typically, and a complementary female cone placed over it and gently dropped to form the legs 3, 4 and 5 of the metal assembly 1 in the correct position. Normally, the blank will be sheathed in argon gas during the forming process to avoid surface hardening and oxidation.

After removing the blank (i.e. the partly shaped metal assembly) from the cone, it is further deburred, placed on a second forming mandril at the same temperature and a second forming process is carried out which ensures that the base ring and the legs are accurately shaped.

The metal assembly is then removed and inspected and placed on a third forming jig which holds the base ring but forms the legs to produce the final shape required. Next, it is removed, cleaned, examined and etched to remove any possible surface contamination. A careful examination of the edges is made to ensure that no cracking can take place.

At this stage the metal assembly can be tested to ensure that each leg has the required flexibility, by determining the aforementioned radial load required to deflect the respective ends 9, 10 and 11 by 1 mm. As mentioned above, the load generally should be within the range 50 g to 150 g, preferably from 70 g to 90 g. We prefer to design the blanks so that the thickness of the length of metal 6 (which as explained previously varies smoothly along its length) will, if off specification at all, be too great. Then one can adjust the flexibility of the legs 3, 4 and 5 down to the required level by dipping them into an etching solution. By way of example, we believe the optimum value of the aforementioned radial load for each leg of a metal assembly 1 having a base ring 2 of 26 mm outside diameter is 80 g. The metal assembly 1 is finally cleaned, washed and further inspected.

We very much prefer that the base ring should be substantially rigid (as herein defined). Preferably, the base ring is sufficiently rigid that it requires a radial force of at least 200 g applied to the base ring to cause it to move radially inwardly by a distance of 1 mm. More preferably, the aforementioned radial force applied to the base ring is at least 210 g. Thus, for example, when testing the rigidity of the base ring 2 of the metal assembly 1 shown in FIG. 1, the size of the assembly being such that the base ring 2 has a 26 mm outside diameter, we mount the assembly with the base ring 2 in a substantially vertical plane and one of the connecting pieces 12, 13 or 14 supported by a horizontal surface, and we determine the radial load applied inwardly to the diametrically opposite point on the base ring 2 required to cause a 1 mm deflection; the assembly passes the test (in accordance with the most preferred embodiment) if this load is at least 210 g.

What is claimed is:

1. A stent for a cardiac valve, the stent having an axial direction, a metal base ring disposed generally radially about said axial direction, and metal legs, for attachment of commissures or cusps of a valve, projecting from the base ring generally in said axial direction, wherein said legs are flexible such that in use they bend resiliently along substantially the whole of their axial length to take up strain in a valve mounted in the stent when the valve closes without substantially impairing the performance of the valve.

2. A stent as claimed in claim 1, wherein the legs are formed by a length of metal which smoothly rises and falls around the circumference of the stent and is connected to the base ring solely at the points of closest approach of the length of metal to the base ring.

3. A stent as claimed in claim 2, wherein the thickness of the metal forming the legs decreased with increasing distance from the base ring.

4. A stent as claimed in claim 3, wherein each leg curves inwardly towards the axis of the stent, being concave to the axis and furthest from said axis proximal of the base ring, and nearest to said axis distal of the base ring.

5. A stent as claimed in claim 4, wherein the base ring is substantially rigid such that in use there is no substantial deformation of the base ring.

6. A stent as claimed in claim 5, formed from titanium 6Al 4V.

7. A stent according to claim 6, wherein the flexibility of each leg is such that the radial force applied to the end of the leg remote from said base ring required to move the said end a distance of 1 mm towards the valve axis lies within the range of from about 50 g. to about 150 g.

8. A stent according to claim 7, wherein said force lies within the range of from about 70 g. to about 90 g.

9. A stent according to claim 8, wherein the rigidity of the base ring is such that the radial force applied to the base ring required to cause it to move radially inwardly by a distance of 1 mm is at least about 200 g.

10. A stent according to claim 9, wherein said length of metal is cloth-encased and wherein only the outer periphery of the stent is cloth-covered.

11. A stent according to any one of claims 1 to 10, wherein the metal assembly comprising said metal base ring and metal legs is monolithic and joint-free.

12. A stent according to claim 11, wherein said metal assembly has been made by a process comprising: producing a blank, and forming said blank into the required shape.

13. A stent according to claim 12, wherein said blank has been produced from a sheet of metal.

14. A stent according to claim 13, wherein forming said blank has comprised shaping the blank between male and female members.

15. A stent according to claim 14, wherein the blank has been changed at a temperature of about 950° C. ±50° C. in an inert atmosphere.

16. A stent according to any one of claims 1–10, having a natural or biomaterial valve fitted thereto.

17. A stent according to claim 11, having a natural or biomaterial valve fitted thereto.

18. A stent according to claim 12, having a natural or biomaterial valve fitted thereto.

19. A stent according to claim 13, having a natural or biomaterial valve fitted thereto.

20. A stent according to claim 14, having a natural or biomaterial valve fitted thereto.

21. A stent according to claim 15, having a natural or biomaterial valve fitted thereto.

* * * * *